(12) United States Patent
Buck (10) Patent No.: US 9,381,538 B2
(45) Date of Patent: Jul. 5, 2016

(54) DRIVING DEVICE OF A METERING AND MIXING APPARATUS

(71) Applicant: SIKA TECHNOLOGY AG, Baar (CH)

(72) Inventor: Manuel Buck, Gebenstorf (CH)

(73) Assignee: SIKA TECHNOLOGY AG, Baar (CH)

( * ) Notice: Subject to any disclaimer, the term of this patent is extended or adjusted under 35 U.S.C. 154(b) by 107 days.

(21) Appl. No.: 14/311,968

(22) Filed: Jun. 23, 2014

(65) Prior Publication Data

US 2014/0346190 A1 Nov. 27, 2014

Related U.S. Application Data

(63) Continuation of application No. PCT/EP2012/075192, filed on Dec. 12, 2012.

(30) Foreign Application Priority Data

Dec. 21, 2011 (EP) ..................... 11194922

(51) Int. Cl.
*B67D 7/70* (2010.01)
*B05C 17/01* (2006.01)
(Continued)

(52) U.S. Cl.
CPC ............. *B05C 17/0133* (2013.01); *A61C 5/064* (2013.01); *B01F 13/0023* (2013.01);
(Continued)

(58) Field of Classification Search
CPC .............. B05C 17/0133; B05C 17/00553; B05C 17/00566; B05C 17/00576; B05C 17/00596; B05C 17/0103; B05C 17/014; B05C 17/0116; A61C 5/064; B01F 13/0023; B01F 15/0237; B01F 15/042; B01F 2215/0027; B01F 2215/0039; B01F 13/0027
See application file for complete search history.

(56) References Cited

U.S. PATENT DOCUMENTS 3,570,719 A * 3/1971 Schiff ............... B05C 17/00506
222/137
3,854,629 A * 12/1974 Blieberger .......... B05C 17/0103
222/109

(Continued)

FOREIGN PATENT DOCUMENTS

DE 32 33 366 A1 9/1983
EP 0 057 465 A2 8/1982
(Continued)

OTHER PUBLICATIONS

International Search Report (PCT/ISA/210) mailed on Jan. 18, 2013, by the European Patent Office as the International Searching Authority for International Application No. PCT/EP2012/075192.

(Continued)

*Primary Examiner* — Patrick M Buechner
(74) *Attorney, Agent, or Firm* — Buchanan Ingersoll & Rooney PC (57) ABSTRACT

A driving device of a metering and mixing apparatus for multi-component substances has at least two cartridge holders for holding interchangeable cartridges, a discharging apparatus for the simultaneous discharging of the substance components from the cartridges by discharging pistons entering the cartridge holder or cartridges, where at least one discharging piston has a thread which can generate a forward propulsion of the discharging piston, and a mixing apparatus for discharging the substance components in mixed form. A transmission unit connects a drive motor, and a spindle-like discharging rod of the discharging piston is provided with the thread, a rear part of the longitudinal extent of which discharging rod has a spiral-toothed, non-self-locking spindle section, and at a front end of which has an engagement element for engaging in the discharging piston.

18 Claims, 6 Drawing Sheets

(51) Int. Cl.
   *B05C 17/005* (2006.01)
   *A61C 5/06* (2006.01)
   *B01F 13/00* (2006.01)
   *B01F 15/02* (2006.01)
   *B01F 15/04* (2006.01)

(52) U.S. Cl.
   CPC ............ *B01F15/0237* (2013.01); *B01F 15/042* (2013.01); *B05C 17/0053* (2013.01); *B05C 17/00566* (2013.01); *B05C 17/00576* (2013.01); *B05C 17/00596* (2013.01); *B05C 17/0103* (2013.01); *B05C 17/014* (2013.01); *B01F 2215/0027* (2013.01); *B01F 2215/0039* (2013.01); *B05C 17/0116* (2013.01)

(56) References Cited

U.S. PATENT DOCUMENTS

| | | | | |
|---|---|---|---|---|
| 4,471,888 A | * | 9/1984 | Herb | B05C 17/00553 222/137 |
| 4,653,675 A | * | 3/1987 | Ratzky | B05C 17/0103 222/333 |
| 4,840,294 A | * | 6/1989 | Ernst | B05C 17/0123 222/287 |
| 4,934,827 A | * | 6/1990 | Taschke | B05C 17/00553 222/137 |
| 4,986,443 A | * | 1/1991 | Saur | B05C 17/00553 222/1 |
| 5,104,005 A | * | 4/1992 | Schneider, Jr. | B05C 17/00553 222/137 |
| 5,203,476 A | * | 4/1993 | Keller | B05C 17/0103 222/136 |
| 5,207,357 A | * | 5/1993 | Aronie | B05C 17/00553 222/134 |
| 5,697,524 A | * | 12/1997 | Sedlmeier | B01F 13/002 222/105 |
| 6,311,871 B1 | * | 11/2001 | Binder | B05C 17/00516 222/145.6 |
| 2003/0022128 A1 | | 1/2003 | Heymann et al. | |
| 2003/0123323 A1 | * | 7/2003 | Bublewitz | A61C 5/064 366/172.1 |
| 2006/0283885 A1 | * | 12/2006 | Dolman | B05C 17/00553 222/135 |
| 2008/0144426 A1 | | 6/2008 | Janssen et al. | |
| 2008/0251535 A1 | * | 10/2008 | Suchan | A61C 5/064 222/83 |
| 2009/0039113 A1 | | 2/2009 | Hsu et al. | |
| 2010/0091607 A1 | * | 4/2010 | Meyer | A61C 5/064 366/151.2 |
| 2010/0288790 A1 | * | 11/2010 | Keller | A61B 17/00491 222/39 |
| 2012/0148980 A1 | | 6/2012 | Gramann et al. | |
| 2013/0277390 A1 | | 10/2013 | Buck et al. | |
| 2013/0277393 A1 | * | 10/2013 | Rahm | B05C 17/00503 222/137 |
| 2014/0092704 A1 | | 4/2014 | Janssen et al. | |
| 2014/0301156 A1 | * | 10/2014 | Rahm | B05C 17/00566 366/184 |
| 2014/0346190 A1 | * | 11/2014 | Buck | B05C 17/0133 222/137 |
| 2014/0346251 A1 | * | 11/2014 | Schultheiss | B05B 7/24 239/314 |

FOREIGN PATENT DOCUMENTS

| | | |
|---|---|---|
| EP | 1 279 379 A1 | 1/2003 |
| EP | 2 468 415 A1 | 6/2012 |
| WO | WO 2008/076941 A1 | 6/2008 |
| WO | WO 2011/025831 A1 | 3/2011 |

OTHER PUBLICATIONS

Written Opinion (PCT/ISA/237) maiied Jan. 18, 2013, by the European Patent Office as the International Searching Authority for International Application No. PCT/EP2012/075192.
International Search Report (PCT/ISA/210) mailed on Jan. 24, 2013, by the European Patent Office as the International Searching Authority for International Application No. PCT/EP2012/075155.
Written Opinion (PCT/ISA/237) mailed on Jan. 24, 2013, by the European Patent Office as the International Searching Authority for International Application No. PCT/EP2012/075155.
International Search Report (PCT/ISA/210) mailed on Feb. 5, 2013, by the European Patent Office as the International Searching Authority for International Application No. PCT/EP2012/076508.
Written Opinion (PCT/ISA/237) mailed on Feb. 5, 2013, by the European Patent Office as the International Searching Authority for International Application No. PCT/EP2012/076508.
Notification of Transmittal of Translation of the International Preliminary Report on Patentability (Forms PCT/IB/338 and PCT/IB/373) and the Written Opinion of the International Searching Authority (Form PCT/ISA/237) issued on Jul. 3, 2014, by the International Bureau of WIPO in corresponding International Application No. PCT/EP2012/075192. (10 pages).

* cited by examiner

DRIVING DEVICE OF A METERING AND MIXING APPARATUS

RELATED APPLICATION(S)

This application claims priority as a continuation application under 35 U.S.C. §120 to PCT/EP2012/075192, which was filed as an International Application on Dec. 12, 2012 designating the U.S., and which claims priority to European Application 11194922.8 filed in Europe on Dec. 21, 2011. The entire contents of these applications are hereby incorporated by reference in their entireties.

FIELD

The disclosure relates to a driving device of a metering and mixing apparatus for multi-component substances, for example, multi-component adhesives, which can have at least two interconnected cartridge holders for holding replaceable cartridges with individual substance components, a discharge device for simultaneously discharging the substance components from the cartridges through component outlets by discharging pistons that enter the cartridge holder or cartridges, wherein at least one discharging piston has a threading which by rotating can create forward propulsion of this discharging piston, and which can have a mixing apparatus which can be connected to the component outlets and mix the discharged substance components and dispense them in a mixed state.

BACKGROUND INFORMATION

A metering and mixing apparatus is disclosed in European Patent Application 10 196 972.3 of the applicant.

A similar metering and mixing apparatus for mixing a dental impression compound is already known from DE 3 233 366 A1. This device includes a stirring unit, designed as a disposable part, with a base body that has a mixing chamber with several feed channels opening separately into the mixing chamber for the components of the impression compound and an outlet opening for the mixed impression compound. The stirring unit also has a stirrer, arranged rotatably in the mixing chamber, which is driven by a driving device against which the stirring unit is held removably. The components of the impression compound are held in reservoir cylinders and are forced by pistons into the mixing chamber, and after mixing are forced out through the outlet opening into the impression tray. The speed of advance of the actuating drives of the pistons can be varied so that both the ratio of the piston advance speed, which determines the setting time of the impression compound and the overall advance or the duration of advance and thus the quantity of impression compound, can be controlled.

Reference is also made to EP 0 057 465 A2, WO 2011/025831 A1, US 2009/039113 A1, WO 2008/076941 A1 and EP 2 279 379 A1.

SUMMARY

A driving device of a metering and mixing apparatus for multi-component substances is disclosed, the driving device comprising: at least two cartridge holders configured to hold replaceable cartridges with individual substance components; a discharging device configured to simultaneous discharge the substance components from cartridges through component outlets with aid of discharging pistons for entering the cartridge holder or cartridges, wherein at least one discharge piston has a threading which will produce forward propulsion of the at least one discharge piston by rotation; a mixing apparatus connected to the component outlets for mixing the discharged substance components and discharging them in mixed form; a spindle-like discharging rod of the at least one discharging piston provided with the threading, which in a rear part has a spiral-toothed spindle section and at a front end has an engagement element for engaging in the at least one discharging piston; and a transmission unit for connection of a drive motor, wherein the transmission unit has an internally toothed driven wheel which is matched to the spiral toothing of the spindle section.

A device for multi-component substances is disclosed, the device comprising: an integrated electric driving motor; a battery power supply for the integrated electric driving motor; and a driving device, which includes: at least two cartridge holders configured to hold replaceable cartridges with individual substance components; a discharging device configured to simultaneously discharge the substance components from cartridges through component outlets with aid of discharging pistons for entering the cartridge holder or cartridges, wherein at least one discharge piston has a threading which will produce forward propulsion of the at least one discharge piston by rotation; a mixing apparatus connected to the component outlets for mixing the discharged substance components and discharging them in mixed form; a spindle-like discharging rod of the at least one discharging piston provided with the threading, which in a rear part of its longitudinal extent based on a position of use has a spiral-toothed spindle section and at a front end has an engagement element for engaging in the at least one discharging piston; and a transmission unit for connection of a drive motor, wherein the transmission unit has an internally toothed driven wheel which is matched to the spiral toothing of the spindle section.

BRIEF DESCRIPTION OF THE DRAWINGS

The disclosure will now be further explained by way of exemplary embodiments and with reference to the accompanying drawings, in which.

DETAILED DESCRIPTION

A driving device of a metering and mixing apparatus for multi-component substances is disclosed, for example, for multi-component adhesives, which can have at least two interconnected cartridge holders for holding replaceable cartridges with individual substance components, a discharge device for simultaneously discharging the substance components from the cartridges through component outlets by discharging pistons that enter the cartridge holder or cartridges, wherein at least one discharging piston has a threading which by rotating can create forward propulsion of this discharging piston, and which can have a mixing apparatus which can be connected to the component outlets and mix the discharged substance components and dispense them in a mixed state.

In accordance with an exemplary embodiment, in the propulsion of a metering and mixing apparatus using a self-cutting drive piston, the piston can continuously be in a positive force-transferring connection with a drive motor. In accordance with an exemplary embodiment, the propulsion of the metering and mixing apparatus can use a spiral-toothed, non-self-locking spindle drive. The disclosure also includes providing a transmission unit, the driven wheel of which has teeth matched to the teeth of the discharging rod with spindle section. In addition, the disclosure includes providing an engagement element at the front end (in the position of use) of the said discharging rod for engaging in the discharging piston. With the suggested solution, for example, a drive force can be coupled independently into a piston, for example, a self-cutting piston, that generates a forward drive independently. This can be accomplished where, in the case of parallel discharging of (at least) one other component, which can take place via a known discharge piston, a predetermined (counter) pressure threshold can be exceeded. According to many types of use, the discharge of the components with the self-cutting piston can be suppressed when, and for as long as another component to be mixed with the first-mentioned one is not being discharged simultaneously. In addition, when reloading the metering and mixing apparatus, the discharging rod of the self-cutting piston can be brought pack into its starting position again simply by pushing back, for example, without appreciable resistance and without additional manipulations.

In accordance with an exemplary embodiment, a metering and mixing apparatus as disclosed, with (at least) one discharging piston automatically generating forward propulsion by rotation, where no appreciable axial force is supplied for this, but merely a sufficient rotational momentum. For example, the axial force should only be large enough so that the discharging rod does not lose contact with the discharging piston.

In accordance with an exemplary embodiment, the driving device can include a spirally-toothed spindle section, which can exhibit a high lead of the spiral toothing of between 45° and 65°, for example, between 50° and 61°.

In accordance with an exemplary embodiment, the engagement element at the end of the discharging rod can be a polygonal element, Torx or claw element. For example, the shape of the engagement element can correspond to the shape of a corresponding projection or inset molding on the back side (in the position of use) of the driving piston at least insofar as is necessary for transferring the torque levels required in the instance of use. For example, the geometric shape of the engagement element and the engagement opening need not necessarily be identical. In an exemplary embodiment, the engagement element corresponding to an engagement fitting on the discharging piston can be self-locating. In accordance with an exemplary embodiment, "idling" phases of the drive and damage to the engagement area of the discharging piston can be largely avoided.

In an accordance with an exemplary embodiment, the spindle-like discharging rod can comprise, for example, essentially of steel, and the engagement area of the discharging piston can comprise, for example, essentially of plastic. However, other material pairs can be used, and can be reasonable for special applications, for example, the spindle can, for example, consist of, as a whole or in part, a nonferrous alloy, such as brass or bronze or an aluminum alloy, and in the discharging pistons as well, known to be made essentially of plastic, a counter-piece also made of metal can optionally be used for the spindle engagement element.

In an exemplary embodiment, the spindle-like discharging rod can be made essentially of steel and the inner, toothed driven wheel can be made essentially of plastic. In accordance with an exemplary embodiment, other material pairings, according to the above-mentioned examples, for example, can be used.

In an exemplary embodiment, a following braking element can be provided in the front end of the discharging rod, and outside of the spiral-toothed spindle section. The features of the metering and mixing device for which the suggested driving device is intended, can ensure the supplying of an axial force (discharging force) under a load, thus in the coupled-in state of the discharge spindle in the discharge piston. However, additional means can be provided in order to generate an axial motion in the idle state as well, which ultimately also means that the discharging rod can locate the discharge piston. The braking element mentioned can ensure this.

In an exemplary embodiment, the moving braking element can be a moving plastic brake. In an exemplary embodiment, the moving braking element can be configured as a following wrap spring housing.

In accordance with an exemplary embodiment, of the metering and mixing device, is possible to determine whether the discharge piston provided with the thread is operating correctly, and is actually being moved forward and as a result, discharging the appropriate component, an exemplary embodiment has on the discharging rod of the discharge piston provided with the thread a position marking element for, exemplary optical detection of the axial position of the discharging rod and thus indirectly of the discharging piston. In an exemplary embodiment expeditiously combining the above-mentioned aspects of execution, it is provided that the position marking element is formed by the carrying along of the braking element or is attached to it.

In an exemplary embodiment, the transmission unit can be a planetary transmission unit (of the driving motor), which has a primary driven wheel. For example, a switchable coupling apparatus can be provided, which can include a coupling element with a driving pinion gear engaging with the primary driven wheel, and can include an additional coupling element that can be designed as an internal spiral toothing for the transmission unit.

In accordance with an exemplary embodiment, the above-mentioned desirable connection of the discharge of the component discharged with the self-cutting discharging piston to the simultaneous discharging of (at least) one additional component can be accomplished with particular reliability in an exemplary embodiment of the disclosure. In this, the transmission unit can be structured for driving the discharging piston provided with the threading and at least one additional discharging piston for another component, driven over a gear rack, and it can have an axially movable gear assembly that can be movable axially under counter-pressure during discharging of the other component. In this connection, the one coupling element of the switchable coupling device can be positioned essentially fixedly in the axial direction relative to the movable assembly, such that it moves with this assembly under the counter-pressure during discharging of the other component. As a result, the first coupling element engages with the other coupling element, fixedly disposed relative to the apparatus housing.

The framework of the present disclosure can also include an application apparatus for multi-component substances, for example, for multi-component adhesives, with a driving device as disclosed herein, with an integrated electric driving motor and battery power supply for this as well as an operating and control unit.

Figure 1:
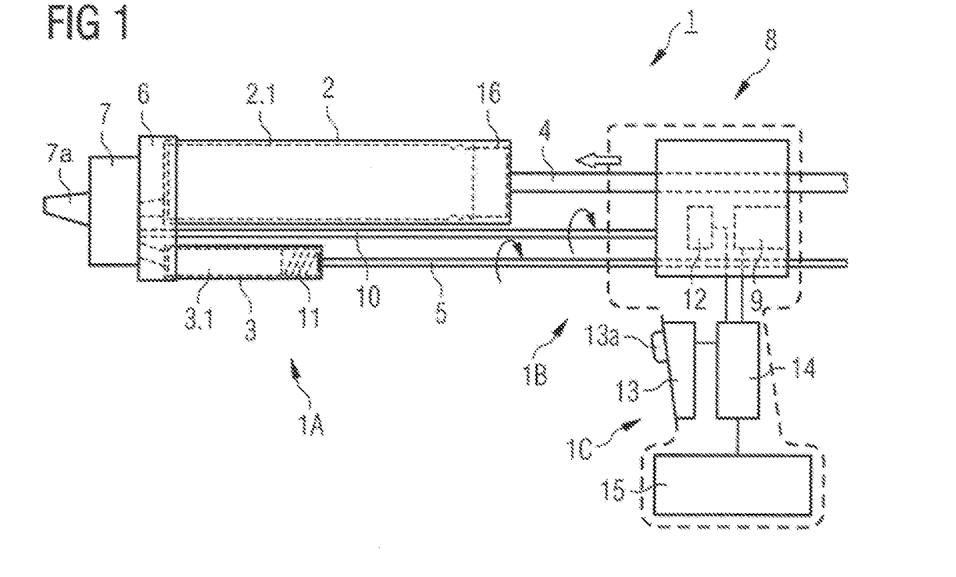
FIG. 1 is side view of an exemplary application device according to the disclosure for a 2-component adhesive.

FIG. 1 shows a side view (schematic representation) of an exemplary application device 1 according to the disclosure, wherein a metering and mixing apparatus 1A, a corresponding drive device 1B, and an apparatus body 1C can be separately designated as components.

The metering and mixing apparatus 1A can include, shown as examples, two cartridge holders 2 and 3 with different diameters and different lengths for a tubular sack 2.1 and a solid cartridge 3.1. The larger cartridge holder 2 can be actuated with an axially movable first drive piston ("linear piston") 16 that can be connected to a first discharging rod (gear rack) 4 and can be advanced by this in a linear fashion into the cartridge holder 2. The cartridge holder 3, which has a substantially smaller diameter and also is substantially shorter than the cartridge holder 2, according to the disclosure can be actuated by a second drive piston ("rotary piston"), which on its outside has a threading that engages with the inner wall of the cartridge holder 3 or a cartridge 3.1 inserted therein and can generate forward drive by rotation.

The drive unit 1B can include a transmission unit 8, which can have a single drive inlet side and three different drive outlet sides. The drive outlet sides can be an outlet for the linearly advanced gear rack 4, or an outlet for a second discharging rod 5 and an outlet for a likewise rotating drive shaft 10, which can operate a rotary mixer 7. The two cartridge holders 2 and 3 on the discharge side can be connected with a cartridge coupling 6, through which the substance can be present in the cartridge holders 2 and 3 can be delivered from the component outlets to the rotary mixer 7, which can be connected to the cartridge coupling 6. The design of such a rotary mixer is known. For example, the rotary mixer can have a drive tip 7a attached at the front, through which the mixed substance can ultimately be discharged.

The transmission unit 8 in the embodiment of the metering and mixing apparatus 1 shown in FIG. 1 can be driven with the aid of an electric motor 9. A microswitch 12 can be provided, the function of which will be described further below. The device body 1C can include an operating unit 13 with a manually actuatable on and off switch 13a, a drive control unit 14 and a battery pack 15.

Figure 2:
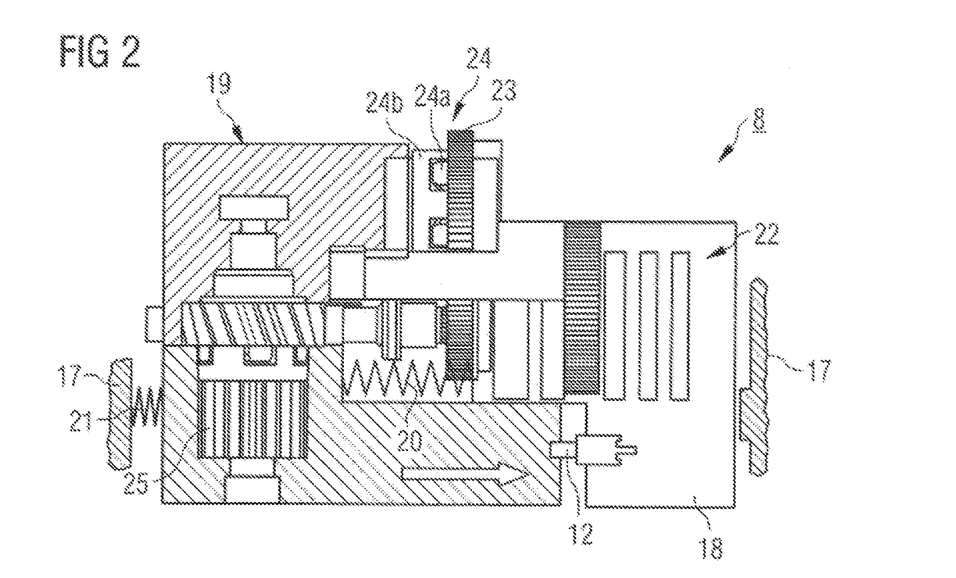
FIG. 2 is a representation of an exemplary structure of a transmission unit of the exemplary application device according to FIG. 1.
Figure 6:
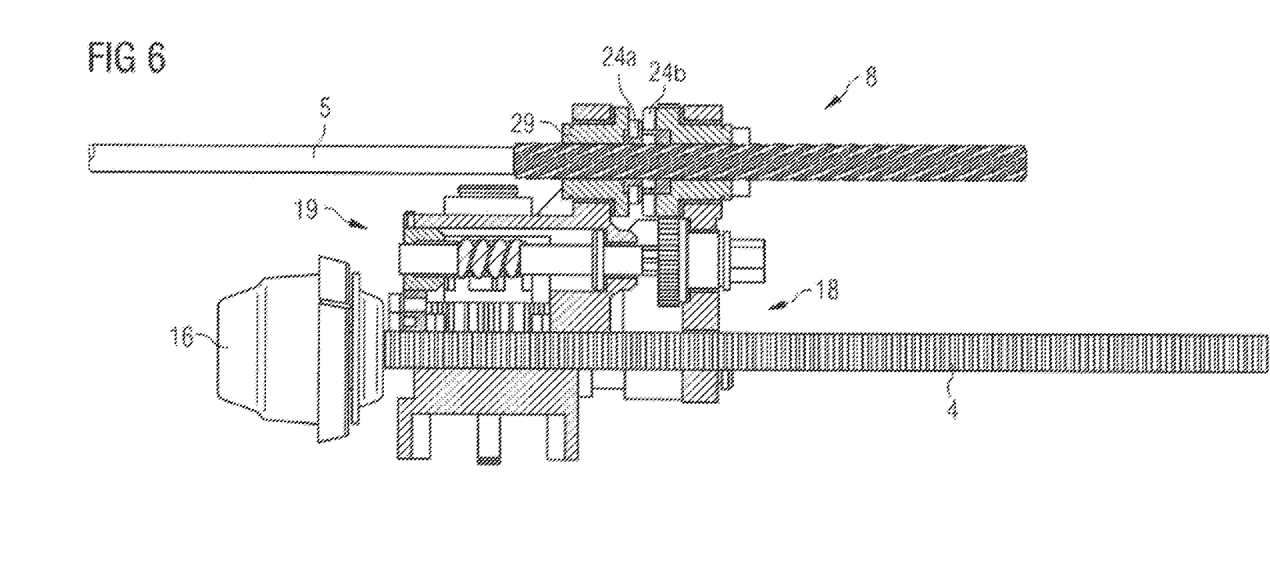
FIG. 6 is a cutaway view of an exemplary embodiment of the transmission unit of the application device according to FIG. 1.

FIGS. 2 and 6 show the structure of an exemplary embodiment of the transmission unit 8. The method of presentation of FIG. 2 and additional figures differs from that in FIG. 1 in that in FIG. 2, the gear components forming part of the gear rack 4 can be at the bottom and the components belonging to the second discharging rod 5 can be located at the top.

The transmission unit 8 can include a first assembly 18 fixed in place relative to a wall of an apparatus housing 17 of the application device and a second assembly 19 carried movably in the apparatus housing. The two gear assemblies 18 and 19 can be clamped elastically together by means of a counter-pressure spring 20 (shown here symbolically) and the movable assembly 19 can be elastically supported against the apparatus housing 17 with an additional spring element 21, which can also be designated as a pressure spring element in the remainder of the document. The first assembly 18 can include a planetary gear 22, which can be in contact with a drive pinion of the drive motor, and the output 23 for driving the spindle-like second drive rod and driven gears for the first discharging rod (gear rack) and the drive shaft of the mixer.

At the output for the second discharging rod, a switchable coupling (e.g., claw coupling) 24 can be provided, which can include a first coupling element 24a fixed in place relative to the first assembly 18 and a second coupling element 24b fixed in place relative to the second assembly 19. A gear component 25 placed in the second assembly 19 for driving the first discharging rod (gear rack) will be described herein.

A microswitch 12 can be fixed on the first assembly 18 and can be positioned such that the microswitch can be actuated in a preset movement position of the second assembly 19.

The functioning of the two-part design of the transmission unit 8 with the spring supports mentioned and the microswitch is as follows in a simplified description:

In the switched-off state of the application device, the second assembly 19 can advance forward relative to the first assembly 18 of the transmission unit 8 due to the force of the counter-pressure spring 20 that the first and second coupling elements 24a, 24b of the switchable coupling 24 are not connected and the second assembly also does not touch the microswitch 12. The exact resting position of the second assembly 19 can be adjusted by suitable selection of the back-pressure spring 20 and the forward-pressure spring 21, adapted to one another, and the response behavior of the mounting of the second assembly on startup of the apparatus.

On startup, the drive force can proceed from the drive motor over the planetary gear 22 and the gear component 25 to the gear rack 4 and can cause it to move in the drive direction of the metering and mixing apparatus (to the left in FIG. 1 and FIG. 2). As soon as the first discharging piston 16 encounters the end of the filled cartridge 2.1 facing it, a reactive pressure builds up, because of the viscosity of the substance component contained therein and is transmitted over the gear rack 4 to its drive pinion (see FIG. 3A) and is transmitted over its mounting to the second component 19. It causes movement of the second assembly 19 relative to the first assembly 18 against the spring force of the counter-pressure spring 20. As soon as a certain shift amount is reached, the coupling elements 24a, 24b engage, and the flow of force from the drive motor can also reach the spindle-like second discharging rod 5, setting this into rotation and driving the self-cutting piston. At the same time the microswitch 12 is actuated by the movement of the second assembly 19; for the function connected with this process is described herein.

As a result of this design and the resulting sequence it can be relatively ensured in an exemplary embodiment that discharge of the component B contained in cartridge 3.1 takes place only if the component A of the multi-component system contained in cartridge 2.1 is also discharged. This is also true if a partially emptied cartridge with component A is placed in the device at point 1 and the operation is started in the fully retracted initial position of the gear rack 4. For example, this then moves forward in idle mode, and the second gear assembly 19 remains in the outlet state shifted relative to the first assembly 18, until the first discharging piston 16 encounters the end of the partially filled cartridge. At this time, a reaction force built up there, which presses the second assembly 19 against the first assembly 18 and thus closes the switchable coupling 24, so that the drive force is also introduced into the second discharging rod (spindle) 5. In this application as well, therefore, component B is only discharged at the correct time.

Figure 3A:
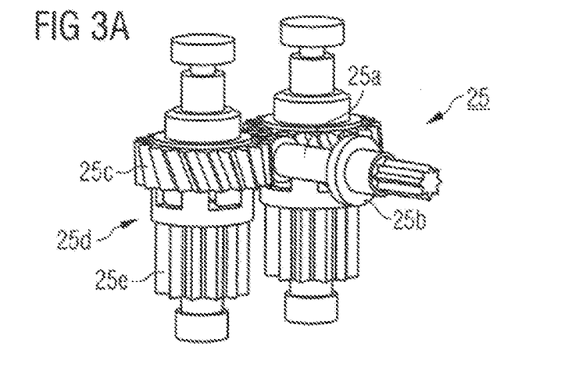
FIGS. 3A and 3B are perspective views of an exemplary embodiment of transmission component serving to drive the gear rack.
Figure 3B:
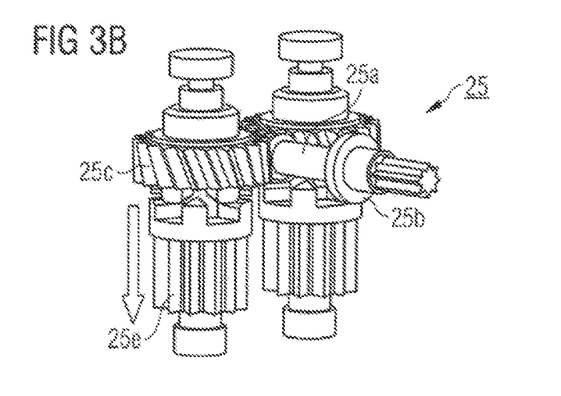

FIGS. 3A and 3B show, as an exemplary embodiment of the gear component serving to drive the first discharging rod (gear rack 4), a coupling-capable screw drive 25 in the coupled-in (FIG. 3A) and uncoupled (FIG. 3B) states. The screw drive includes a screw 25a with a spline shaft which is supported in an axial bearing 25b and is driven over a drive gear (not shown here) of the planetary gear. Two worm gears 25c with helical teeth can be engaged with the screw 25a, with a claw coupling 25d assigned to each of them. With the displaceable coupling element of this coupling 25d in each case a straight-toothed drive pinion 25e is fixed on, which in the engaged state of the coupling 25d moves along with the worm gear 25c and transmits the drive force to the gear rack (no. 4 in FIG. 1), not shown here, with which it meshes. In the disengaged state shown in FIG. 3B the pinions 25e essentially rotate freely, so that the gear rack supported between them and engaging with them can be moved axially practically without resistance. This makes it possible to easily draw back to reload the application device with a full cartridge 2.1 (FIG. 1).

Figure 4:
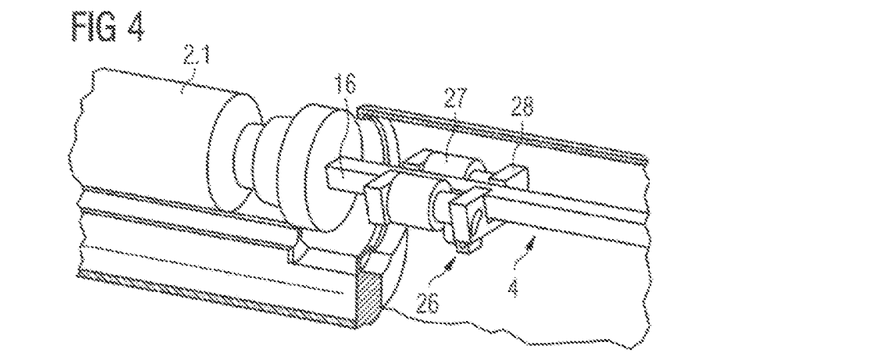
FIG. 4 is a schematic diagram of an exemplary drive of the gear rack.

FIG. 4 shows a schematic diagram in the form of a perspective view of an exemplary drive of the gear rack as shown in FIG. 1. The gear rack 4 can be driven over a spur gear 26 and two screws 27, which can be pivotably supported in a guide bar 28. By pivoting this screw 27 by means of an actuating lever, its engagement with the gear rack 4 can be undone, such that the gear rack can be withdrawn without resistance. In an exemplary embodiment, the gearing part can also be provided such that the gear rack 4 can be driven over two pinions directly meshing in the flanks thereof, with their rotational axes perpendicular to the length of the gear rack. This drive concept is familiar to those skilled in the art and therefore will not be illustrated or described in greater detail.

Figure 5:
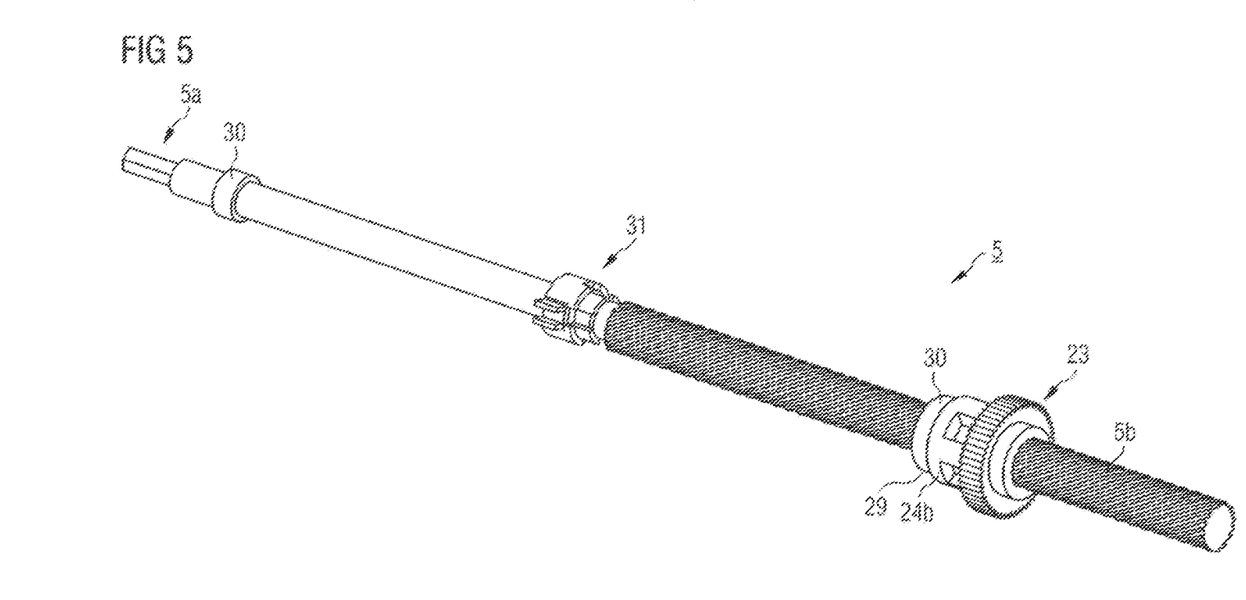
FIG. 5 is a perspective view of an exemplary embodiment of the second discharging rod of the application device according to FIG. 1.

FIG. 5 shows a perspective view of an exemplary embodiment of the second discharging rod 5. As shown in FIG. 5, the second discharging rod 5 at its end (on the left in the figure) can have an engaging element 5a, which can be a polygon for engaging in a correspondingly-shaped engagement device on the discharging rod piston 11 (FIG. 1), which represents a separate part from the discharging rod and for example can be part of the cartridge 3.1 and can be delivered with it. The opposite end section 5b of the discharging rod 5 can have a spiral toothed system with a high lead, resulting in non-self-locking behavior. In this terminal section 5b the spindle-like discharging rod engages with an inner-toothed drive gear 29 of the transmission unit corresponding to the exterior threading of section 5b, which can be fixed to or made in one piece with the second coupling element 24b of the switchable coupling 24 shown in FIG. 2 as described herein.

The drive rod or spindle 5 can be supported at the bearing points 30. Between the end provided with the engaging element 5a and the spiral-toothed end section 5b, the drive rod or spindle 5 can include a cylindrical axis and in this area has a following braking device 31 for generating a minimal braking torque (in the range of 0.5 to 1.0 Nm), which can also generate an axial advance when idling, for example, in the non-engaged state of the discharging rod with the corresponding discharging piston. The braking element 31 can also serve as a position marker for labeling the axial position of the discharging rod in the field of view of an operator or for an optical detection device or can bear such a marking element. In accordance with an exemplary embodiment, the second discharging rod (like the first discharging rod) is moving forward, and thus whether correct discharging of component B is taking place. Thus failure caused, for example, by lack of correct engagement between the discharging rod and the separate discharging piston, can be recognized relatively immediately and the occurrence of incorrect adhesion points can be suppressed.

FIG. 6 shows a sectional view of additional essential parts of the transmission unit 8 with the discharging rods 4 and 5 in place to make their position assignment clear. With regard to the screw drive 25' for driving the first discharging rod 4, the construction can be modified versus the gear component 25 sketched in FIG. 2 as well as FIGS. 3A and 3B.

Figure 7A:
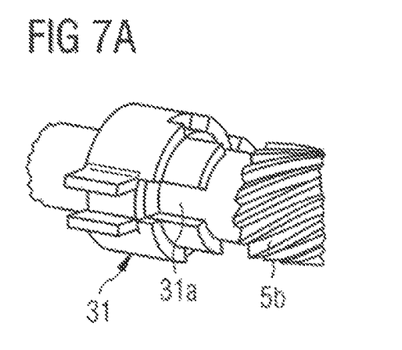
FIGS. 7A and 7B are schematic diagrams in the form of perspective views of an exemplary second discharging rod according to FIG. 5.
Figure 7B:
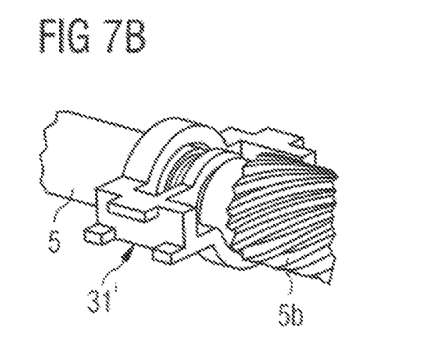

FIGS. 7A and 7B on one hand show in somewhat further detail the braking element 31 already illustrated in FIG. 5, which is designed here as a following wrap spring housing, and the wrap spring 31a is also visible. FIG. 7B shows an embodiment of the braking element as a following plastic brake 31'. Both brake element designs can be already known to those skilled in the art.

Figure 8:
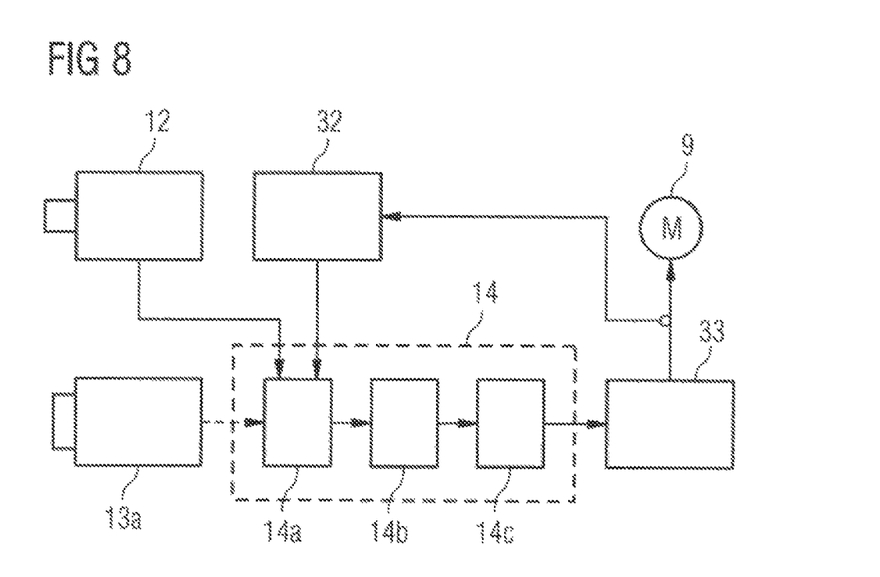
FIG. 8 is a block diagram of an exemplary embodiment of a sensor that forms part of the drive device 1B of the application apparatus according to FIG. 1.

FIG. 8 shows schematically on a block diagram the structure of a sensor system and the associated control means of the proposed drive device. The sensor system, in addition to the previously-mentioned microswitch 12, can include on the on/off switch ("trigger") 13a, serving as the primary operating element, or in addition to this or as a sensory replacement for it, and a current detection unit 32 for detecting the motor current of the drive motor 9, which can be supplied to this over a motor control 33. The drive control unit 14 can include a sensor signal processing step 14a, a delay element 14b, and a control signal outlet step 14c.

A processing algorithm can be implemented in the sensor signal processing unit 14a, where the signals from the microswitch 12, which can contain information on the discharge of component A, can be placed in an appropriate relationship to data originating from the on/off switch 13a or the current detection unit 32 and ultimately provide information on the operating state of the motor. The processing result can be subjected to an appropriate chronological evaluation (likewise based on stored algorithms) in the delay element 14b, and as a result, a suitable motor control signal is emitted in all operating situations of the application device by the control signal output unit 14c.

Figure 9A:
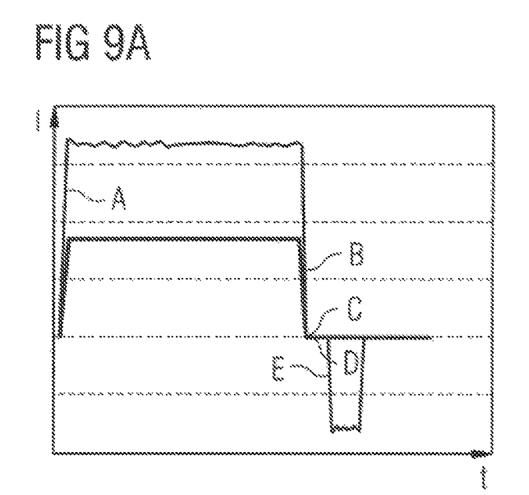
FIGS. 9A and 9B are exemplary machine current-time diagrams for exemplary embodiments of a control sequence of the drive control.
Figure 9B:
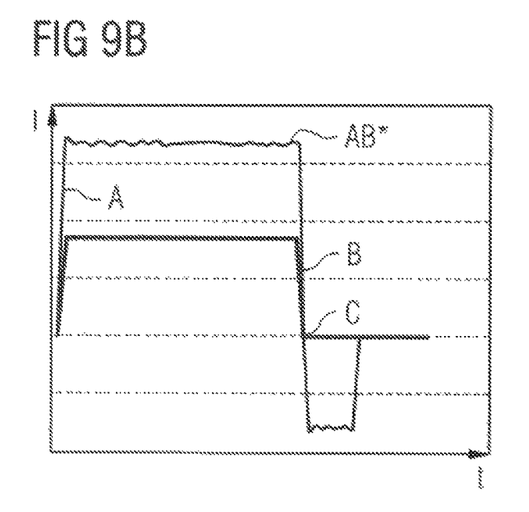

FIGS. 9A and 9B show time sequences based on motor current-time diagrams, which each start at a point A with an increase in the detected motor current I based on a turning-on action of the on/off switch 13a. At point B in FIG. 9A an on/off switch is slowly released; at point C the flow detection unit 32 detects a motor current value of 0, after which, during a brief phase D, the sensor signal processing unit 14a tests whether the motor current remains at the value of 0 to determine whether the on/off switch was released deliberately or accidentally. If the former is the case, then at point E the signal from the still-depressed microswitch 12 can be processed, such that control signal output unit 14c can emit a signal that causes a return stroke of the motor 9.

FIG. 9B shows an alternative version of a comparable control sequence. Here in the sensor signal processing unit 14a before time B (release of the on/off switch) in a phase AB* the motor current value is detected and stored and used for comparison with the current value measured at time point C. Here the processing unit recognizes, based on the comparison result, whether the on/off switch was deliberately released, and as long as a corresponding signal is available from the microswitch 12, starts the motor return stroke at practically the same time.

With the procedure described in both exemplary variants, an unnecessary return stroke of the motor in case of accidental or very brief release of the trigger can be prevented, but at the same time a return stroke that is appropriate because of deliberate termination of the drive process can be initiated, so that an "overshooting" discharge of multi-component substances, especially component A (which would still be under drive pressure if the motor were simply turned off) can be suppressed. At the same time, with the (slight) return stroke and with the end of effect of the reaction force coming from component A the second gear assembly 19 is made to return to its initial position at a maximum distance from the first assembly 18, thus releasing the coupling 24 and the microswitch 12. This can be a suitable shutoff and non-use state of the application device.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A driving device of a metering and mixing apparatus for multi-component substances, the driving device comprising:
    at least two cartridge holders configured to hold replaceable cartridges with individual substance components;
    a discharging device configured to simultaneous discharge the substance components from cartridges through component outlets with aid of discharging pistons for entering the cartridge holder or cartridges, wherein at least one discharge piston has a threading which will produce forward propulsion of the at least one discharge piston by rotation;
    a mixing apparatus connected to the component outlets for mixing the discharged substance components and discharging them in mixed form;
    a discharging rod of the at least one discharging piston provided with the threading, which in a rear part has a spiral-toothed spindle section and at a front end has an engagement element for engaging in the at least one discharging piston; and
    a transmission unit for connection of a drive motor, wherein the transmission unit has an internally toothed driven wheel which is matched to the spiral toothing of the spindle section.

2. The driving device according to claim 1, wherein the spiral-toothed spindle section is a spiral-toothed, non-self-locking, spindle section.

3. The driving device according to claim 1, wherein the spiral-toothed spindle section has a spiral-toothing of between 45° and 65°.

4. The driving device according to claim 3, wherein the spiral-toothing is between 50° and 61°.

5. The driving device according to claim 1, wherein the discharging rod consists of steel and the internally toothed driven wheel consists of plastic.

6. The driving device according to claim 1, comprising:
    a following braking element in a front section of the discharging rod and positioned outside of the spiral-toothed spindle section, the following brake element being configured to provide axial movement of the discharging rod during idling.

7. The driving device according to claim 6, wherein the following braking element is a following plastic brake.

8. The driving device according to claim 6, wherein the following braking element is a following wrap spring housing.

9. The driving device according to claim 1, comprising:
    a position marking element on the discharging rod for optical detection of an axial position of the discharging rod and the discharging piston, which is engaged with the discharging rod.

10. The driving device according to claim 6, comprising:
    a position marking element on the discharging rod for optical detection of an axial position of the discharging rod and the discharging piston when engaged with the discharging rod and wherein the position marking element is formed by or attached to the following braking element.

11. The driving device according to claim 1, wherein the engagement element at the front end of the discharging rod is a polygonal, hexalobular, or claw element.

12. The driving device according to claim 11, wherein the engagement element on the discharging piston is self-locating.

13. The driving device according to claim 1 for combination with a drive motor, comprising:
    a planetary transmission unit of the drive motor having a primary driven wheel; and
    a switchable coupling device, which includes a first coupling element with a drive pinion engaging with the primary driven wheel, and a second coupling element which is the internally toothed driven wheel of the transmission unit.

14. The driving device according to claim 13, wherein the switchable coupling device is a claw coupling.

15. The driving device according to claim 13, wherein the transmission unit is configured to drive the discharging piston having the threading and at least one additional discharging piston for another component, over a gear rack, and has an axially movable assembly which will be under reaction pressure when discharging the other component, and the second coupling element of the switchable coupling device is positioned essentially fixed in an axial direction relative to the movable assembly, and will be under the reaction pressure during discharge of the other component and wherein the discharging piston moves with the movable assembly for engaging with the first coupling element.

16. A device for multi-component substances, the device comprising:
    an integrated electric driving motor;
    a battery power supply for the integrated electric driving motor; and
    a driving device, which includes:
        at least two cartridge holders configured to hold replaceable cartridges with individual substance components;
        a discharging device configured to simultaneous discharge the substance components from cartridges through component outlets with aid of discharging pistons for entering the cartridge holder or cartridges, wherein at least one discharge piston has a threading which will produce forward propulsion of the at least one discharge piston by rotation;
        a mixing apparatus connected to the component outlets for mixing the discharged substance components and discharging them in mixed form;
        a discharging rod of the at least one discharging piston provided with the threading, which in a rear part of its longitudinal extent based on a position of use has a spiral-toothed spindle section and at a front end has an engagement element for engaging in the at least one discharging piston; and
        a transmission unit for connection of a drive motor, wherein the transmission unit has an internally toothed driven wheel which is matched to the spiral toothing of the spindle section.

17. The device according to claim 16, comprising:
an operating and control unit powered by the battery power supply.

18. The device according to claim 16, comprising:
at least one replaceable cartridge with individual substance components.

* * * * *